United States Patent [19]

Pryor

[11] 4,315,688
[45] Feb. 16, 1982

[54] ELECTRO-OPTICAL SENSOR SYSTEMS FOR THREAD AND HOLE INSPECTION

[75] Inventor: Timothy R. Pryor, Tecumseh, Canada
[73] Assignee: Diffracto Ltd., Windsor, Canada
[21] Appl. No.: 64,867
[22] Filed: Aug. 8, 1979
[51] Int. Cl.³ .................. G01B 11/22; G01B 11/04
[52] U.S. Cl. .................. 356/73; 356/378; 356/394; 356/398; 356/430; 356/241; 356/237
[58] Field of Search .............. 356/237, 241, 355, 357, 356/359, 376, 378, 394, 398, 429, 430, 73; 250/562, 563, 572, 577

[56] References Cited

U.S. PATENT DOCUMENTS

| | | | |
|---|---|---|---|
| 3,061,731 | 10/1962 | Thier et al. | 356/430 X |
| 3,404,282 | 10/1968 | Walker | 250/577 X |
| 3,667,846 | 6/1972 | Nater et al. | 250/572 X |
| 3,741,656 | 6/1973 | Shapiro | 250/577 X |
| 3,890,049 | 6/1975 | Collins et al. | 356/429 |
| 3,924,953 | 12/1975 | Allard | 356/394 X |

*Primary Examiner*—Vincent P. McGraw
*Attorney, Agent, or Firm*—Larson and Taylor

[57] ABSTRACT

Method and apparatus for inspecting threaded objects and for determining the depth of blind holes. For inspecting threads, a light source is provided for illuminating threads of a threaded object. A lens forms an image of the illuminated threads. A detector having a light sensitive area sufficiently small to resolve the thread image is provided to detect the image and an output signal is produced in response to the incident image light. The output signal is analyzed to determine the quality of the threads. For determining the depth of a blind hole, a light source forms a spot on the bottom of a blind hole in an object and the lens forms an image of the spot. Means are provided to detect the spot image to produce an output signal responsive to the incident image light. Means are provided to analyze the output signal to determine hole depth.

33 Claims, 9 Drawing Figures

7 THREADS DETECTED

ELECTRO-OPTICAL SENSOR SYSTEMS FOR THREAD AND HOLE INSPECTION

BACKGROUND OF THE INVENTION

The present invention relates to methods and apparatus for inspecting threaded objects and holes.

The inspection of threades and threaded parts is a major problem in modern industry. There are generally two classes of these sorts of inspections that are required. One is to make sure that machines which tap threaded holes in parts such as cylinder heads, engine blocks, exhaust manifolds etc., are indeed performing the job correctly and that the taps have not broken, loaded up, etc. If these things occur, a substantial loss of productivity occurs and additional costs are often incurred down the line for repair.

The second major application of threaded part inspection is inspection of fasteners, bolts, nuts, and other types of items such as rocker studs, etc. In these cases, the ability of the fastener to perform its function and maintain a correct joint can be dependent on the threaded quality. In many cases, the problem does not require measurement of exact threaded dimension: it is sufficient to determine whether or not the threades are present where required.

The invention here disclosed is a simple means of providing inspection of threads and, in particular, threads in blind holes or through holes and is particularly aimed at inspection of nuts and threaded holes in engine components. Also disclosed are means for inspecting holes drilled and otherwise provided in machined parts whose incorrect depth or total absence can lead to loss of productivity and warranty repair or safety related recalls due to lubrication failure, etc.

BRIEF SUMMARY OF THE INVENTION

Apparatus in accordance with the present invention for inspecting threaded objects comprises light source means for illuminating threads of a threaded object, lens means for forming an image of at least a portion of the threads of a threaded object illuminated by the light source means, means for detecting the image, the detecting means comprising a light sensitive member having a light sensitive area sufficiently small to resolve the image of the threads of an illuminated threaded object, the light sensitive member having an output signal responsive to light incident on the light sensitive area, and means for analyzing the output signal to determine the quality of the threads of the threaded object.

A method in accordance with the present invention for inspecting threaded objects comprises providing a sensor unit, the sensor unit comprising light source means for illuminating threads of a threaded object, lens means for forming an image of at least a portion of the threads of a threaded object illuminated by the light source means, and means for detecting the image, the detecting means comprising a light sensitive member having a light sensitive area sufficiently small to resolve the image of the threads of an illuminated threaded object, the light sensitive member having an output signal responsive to light incident on the light sensitive area, moving a threaded object relative to the sensor unit such that the light from the light source means illuminates the threads whereby an image of at least a portion of the threads illuminated by the light is formed by the lens means, and is incident upon the detecting means whereby the output signal is produced, and analyzing the output signal to determine the quality of the threads.

Another aspect of the invention relates to apparatus and methods for the determination of the depth of a blind hole. Apparatus in accordance with this aspect of the invention comprises light source means for projecting a spot of light onto the bottom of a blind hole in an object, lens means for forming an image of the spot of light, detector means for detecting the image, the detector having an output signal responsive to light incident thereon, and means for analyzing the output signal to determine the depth of the hole.

A method in accordance with this aspect of the invention comprises providing a sensor unit, the sensor unit comprising light source means for projecting a spot of light onto the bottom of a blind hole in an object, lens means for forming an image of the spot of light, and detector means for detecting the image, the detector means having an output signal responsive to light thereon, positioning an object having a blind hole such that the spot of light is formed on the bottom of the blind hole, and analyzing the output signal to determine the depth of the hole.

DETAILED DESCRIPTION

There follows a detailed description of a preferred embodiment of the invention, together with accompanying drawings. However, it is to be understood that the detailed description and accompanying drawings are provided solely for the purpose of illustrating a preferred embodiment and that the invention is capable of numerous modifications and variations apparent to those skilled in the art without departing from the spirit and scope of the invention.

FIG. 1 is a diagrammatic side elevation view of an embodiment of the invention;

FIG,. 2 is an enlarged diagrammatic side elevation view of a portion of FIG. 1;

Figure 1:
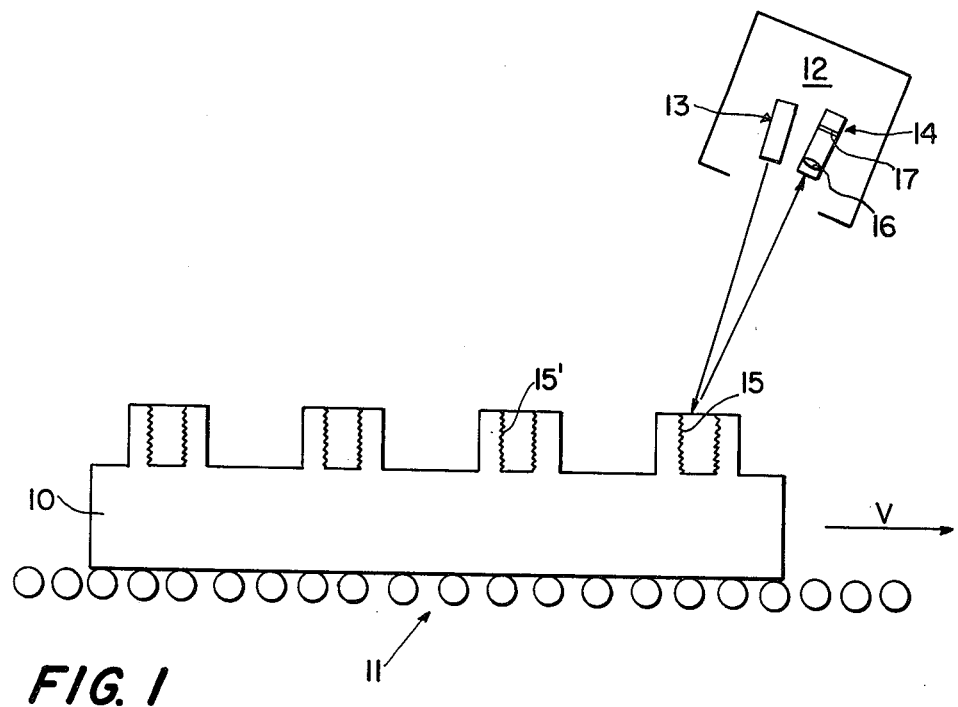
FIG. 1 illustrates the use of the invention in monitoring of the correct number of threads in the various holes in an automotive cylinder head. While the invention also includes a system comprised of a multitude of such sensor heads, each looking down a hole or row of holes, it is of interest to consider for the moment just the operation of one of the heads.
Figure 2:
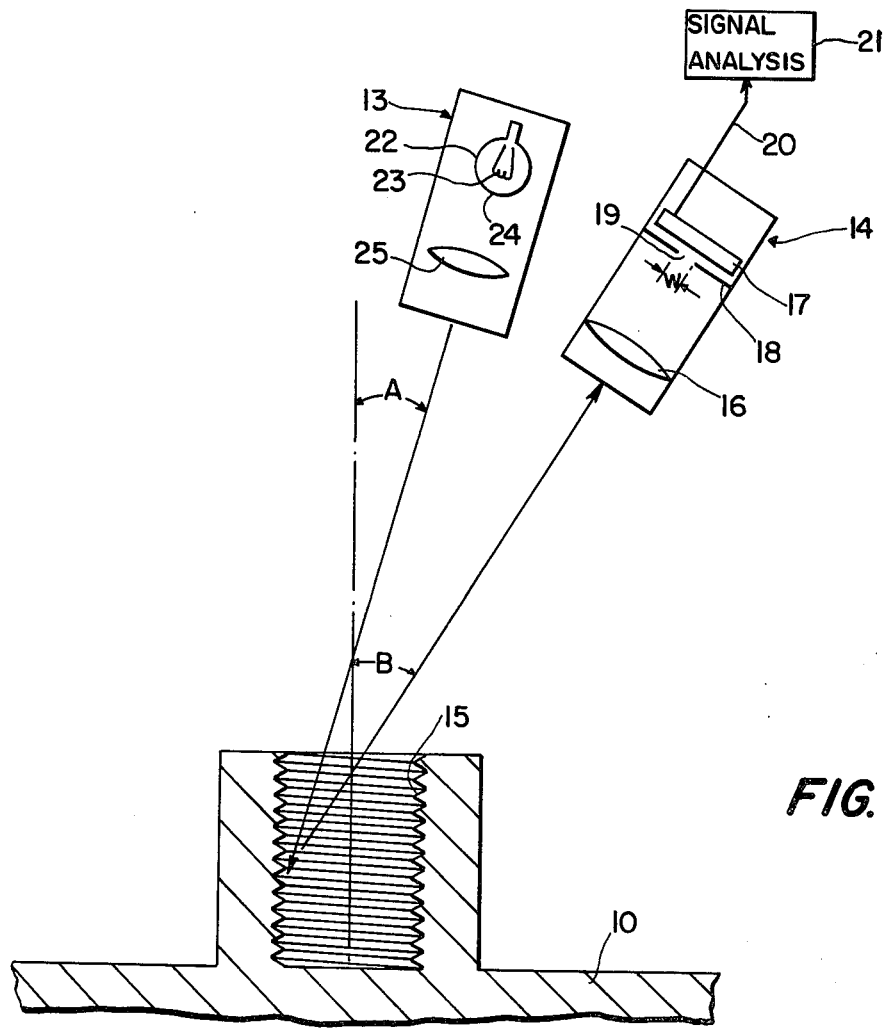

As shown in FIG. 1, a cylinder head 10 or any other part having a threaded portion is conveyed on a driven roller conveyor 11 at a linear velocity "V". A sensor unit 12 is provided for thread inspection and includes a light source unit 13 and a detector unit 14. Light source unit 13 is positioned to illuminate at least a portion of a threaded portion 15 of cylinder head 10. Detector unit 14 includes a lens 16 for forming an image of at least a portion of the threads illuminated by light source unit 13. Detector unit 14 further includes a light sensitive image detector member 17 (see FIG. 2). A mask member 18 is provided closely adjacent to the light sensitive face of detector 17. Mask member 18 has an aperture 19 of size "W" sufficiently small such that the area of detector 17 behind aperture 19 is sufficiently small to resolve the image of the illuminated threads. Light sensitive member 17 has an electrical output signal which is responsive to incident light and which is carried by output head 20 to a signal analysis means 21.

As the part 10 moves through the illuminated area, the light from light source unit 13 illuminates the threaded portions 15, 15', etc. Light source unit 13 is disposed at an acute angle A with respect to the longitudinal centerline of the threaded hole and the light reflected back at acute angle B is thus relatively bright in the area of the inclined sides or flanks of the individual threads and relatively dark in the area of the threads crests. In a preferred arrangement, acute angle A is sufficiently small such that the light reaches the bottom threads in the hole undergoing inspection. It is also preferred that acute angle A is sufficiently small that a shadow of each thread is cast upon the side or flank of the next lower thread. In this embodiment, angle B is chosen larger than angle A so that detector unit 14 is positioned to "see" the shadows as well as the bright reflections. In any event, detector unit 14 is positioned such that lens 16 forms an image of the illuminated threads, the image being formed by the relatively bright and dark areas of reflected light. Light detector 17 is positioned in the image plane of lens 16 and the image is thus incident thereon. The small aperture in mask member 18 reduces the size of the effective area of detector 17 to a size sufficiently small to enable the detector to resolve the individual threads in the thread image incident on the detector. Of course, a smaller light detector may be used, but sufficiently small detectors are expensive and not readily available. It is therefore preferred to use an inexpensive, reliable, readily avaiable detector and mask with a small aperture. Typically, aperture 19 has a width of 0.010" where lens 16 has a focal length of 75 mm.

Aperture 19 is conveniently a slit but may advantageously be curved to conform to the shape of the threads. It will be appreciated that in the thread image formed by lens 19, the alternating bright and dark bands are curved. Where aperture 19 is a slit, a relatively short segment of an individual image band will be incident upon a slit. (It will be remembered that the slit width is sufficiently small to resolve the threads in the thread image.) By using a curved slit of the same width, a good deal longer segment of an image band will be incident on the slit and on the detector thus increasing the detector output signal.

Figure 3:
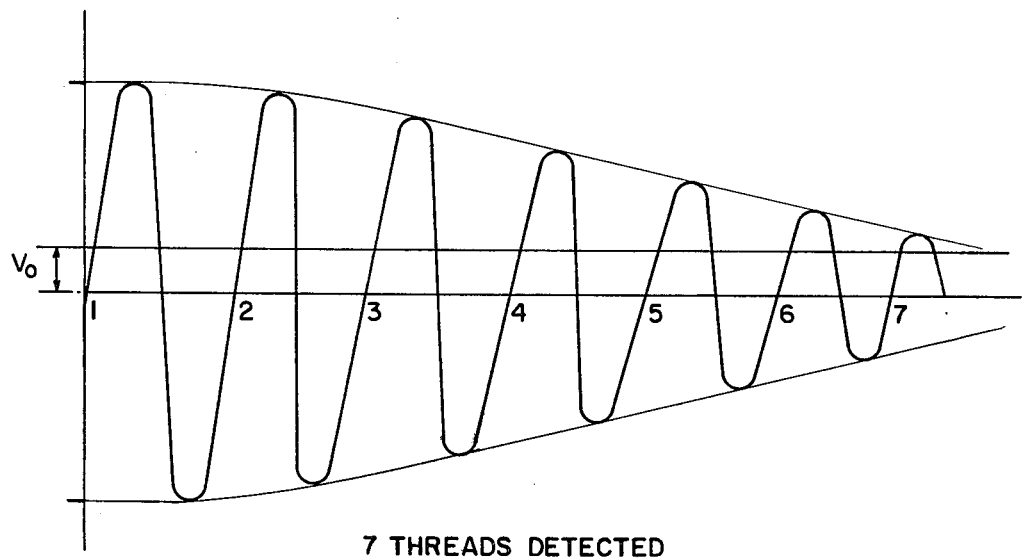
FIG. 3 is a diagrammatic view of a scope trace of an output signal of the embodiment of FIG. 1.

Analysis means 21 are provided for analyzing the electrical output signal produced by detector 17. A typical scope trace of the output signal is illustrated in FIG. 3 which shows the periodic type wave form resulting from inspection of a hole having seven threads. As shown in FIG. 3, the envelope of the thread signal intensity typically dies out somewhat towards the bottom of the inspected hole due to lighting considerations. For a typical situation, e.g., a cylinder head moving at a velocity "V" of 20 inches per second, the thread signal frequency is in the several kilohertz range.

The circuitry of the analysis means is generally set up to simply count the number of threads present and compare the result against a pre-set norm. For example, twelve threads should be present in each of eight cylinder head rocker stud holes. Optionally, an output circuit from this comparison is utilized to feedback to the machining operation and shut down the machine which has made the bad thread.

The thread count is obtained in one embodiment by noting the number of positive going zero crossing of the signal (if AC coupled). Hysteresis and even distinct frequency band pass techniques can be used to ensure that the signal obtained is related to the fixed pitch thread and not stray optical spikes from a cast part surface, for example. Further discrimination is provided by triggering the sensor on and off as described below. use of all these techniques allows one to determine accurately that, for example, there were four holes in the row and each had twelve threads.

To register as a thread count, it is desirable that the optical signal reach at least some set amplitude represented by a value $V_o$ (FIG. 3). However, setting an absolute threshold value can, in some cases, lead to problems in the presence of slight variations in location and in part reflecting properties. Accordingly, it is often desirable, using tapped analog delay lines or the like to provide a floating threshold which follows the envelope of the reflected energy from the threads. A typical envelope is shown in FIG. 3.

Typical reasons for a thread not being present are broken taps which often appear in the holes themselves. Other reasons are that the taps load up which can even cause a missing thread to occur. Optional circuitry can be utilized to find even one missing thread located amongst good threads rather than simply rely on a simple thread count.

It is generally of interest to space these sensor units a suitable distance away from the part to provide clearance. This is particularly true in looking at an end hole as shown, for example, in FIG. 4. Accordingly, relatively long focus lenses are used typically in the range of 50 to 150 millimeters. This allows the detector aperture to be easily made without being unduly small and allows its shape to be tailored if desired to that of the thread image (see below).

In a specific example of the invention as illustrated in FIG. 1, looking at the rocker stud hole of a cylinder head 10, the lens 16 utilized is a Canon 75 mm f 3.5 TV lens, the light detector 17 is an EG&G SG 100 Silicon Photodiode, aperture 19 has a width w of 0.010", and the distance between lens 16 and part 10 is approximately 6". A GE type 1156 taillamp bulb is utilized as a light source 22.

It is an advantage of the present invention that light source 22 may be an inexpensive and readily available light source such as a common automotive bulb. In a preferred embodiment, the light source is an incandescent lamp having a filament 23 and a clear glass envelope 24. Where a light source of this type is employed, a lens 25 is preferably used to focus at least a portion of the filament image on at least a portion of the threads with the lamp filament image aligned co-planar with the hole axis.

It is further noted that the part inspected can be in motion in either direction relative to sensor unit 12, but in a direction sufficiently co-planar with the plane formed by angles A and B and the thread centerline.

It is preferred to turn the sensor on at the correct point such that false thread-like signals are not read from other features of the cylinder head or other part type being inspected. For example, the rough cylinder head castings can sometimes give signals that can be misinterpreted as being threads. Therefore, a part presence sensor is utilized to actuate the analysis means when the cylinder head is in the proper position for that particular thread. Clearly, if there are four such threads in a row, a single sensor head can be used with four such part present heads as shown.

Figure 4:
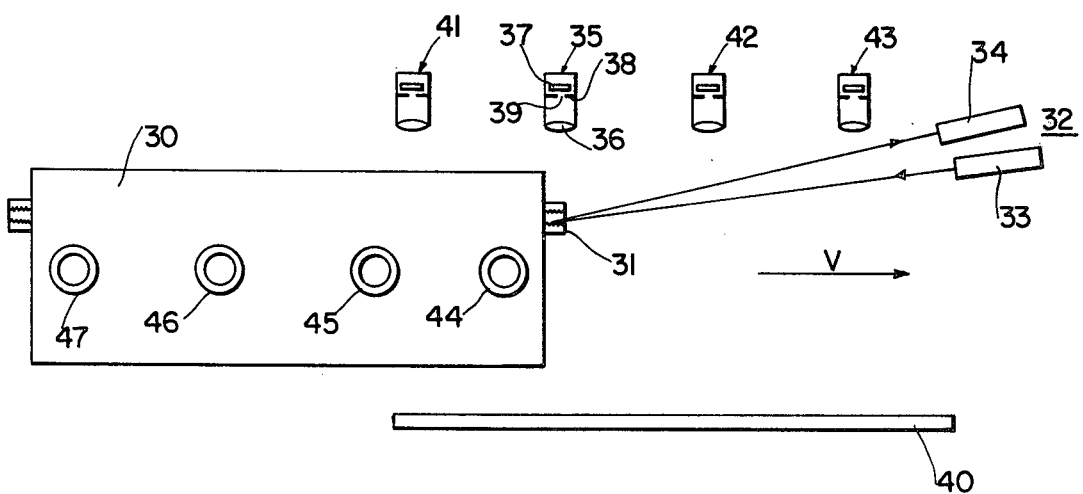
FIG. 4 is a diagrammatic plan view of a further embodiment of the invention.

A suitable part presence sensor is constructed as shown in FIG. 4 in a similar fashion to the thread sensor itself. In FIG. 4, a part 30 is shown in plan view which is similar to part 10 in FIG. 1 but which has an additional threaded hole 31 at the forward (in the sense of the direction of motion of part 30 which is to the right in FIG. 4) end of part 30. A sensor unit 32 of the type described above in connection with FIGS. 1-3 and including a light source unit 33 and a detector unit 34 is provided to inspect threaded end-hole 31. The part presence sensor 35 comprises a lens 36 positioned to image the edge of the part feature used to trigger the readings (e.g. the front of the cylinder head) onto a detector 37 masked by a member 38 having a slit aperture 39. With back illumination in this case, provided by an elongate light 40, the detector sees light until part 30 cuts it off. Typically, a very satisfactory 0.010 to 0.015 inch accuracy is cut off point is easily obtained even with broad light sources such as easily replaced lumaline or other linear lamps which can serve to illuminate several such sensors.

As shown in FIG. 4, more than one part presence sensor can be employed. In the illustrated embodiments, four (35, 41, 42 and 43) are shown. The sensor unit used to inspect threaded top holes 44, 45, 46 and 47 on the top portion of part 30 is arranged as described above in FIGS. 1-3 and is located at a point above hole 45 in FIG. 4 but not shown in the drawing for purposes of illustration. At the moment in time depicted in FIG. 4, the forward edge of part 30 is detected by part presence sensor 35. The output signal generated by the detection of part 30 is used to initiate inspection sensor 32 and to initiate the inspection sensor located above hole 45. A timer may be used to deactuate the sensor units where the velocity V of part 30 is suitable. If desiired, however, additional part presence sensors can be employed to deactuate the inspection sensors. In the illustrated embodiment, a timer (not shown) is used to deactuate the inspection sensors. Sensor 35 is employed to actuate sensor 32 for inspection of end hole 31 and to actuate the top hole inspection sensor for inspection of top hole 45. Sensor 41 is employed to actuate the top hole inspection sensor for inspection of hole 44 which inspection occurred at a time prior to the time illustrated in FIG. 4. Sensor 42 is employed to initiate the top hole inspection sensor for inspection of hole 46 which inspection will occur at a time after the time illustrated in FIG. 4. Similarly, sensor 43 is used to initiate inspection of hole 47.

The apparatus is conveniently provided with an ink marker to mark an inspected part with appropriate information such as an indication of the nature of a detected defect. Additionally, a reject pushoff means can be provided to remove any bad parts from the production line. It is appropriate to point out here that the present apparatus is particularly suitable for installation in a production line and it is contemplated that the apparatus will operate unattended, at normal production rates, with automatic feeding and removal of parts. While a roller conveyor transport mechanism has been shown, it is clear that any other mechanism with relatively continuous motion can be used such as a lift and carry, shuttle, etc. Small parts, such as nuts, are preferably moved on a driven conveyor belt.

The apparatus may be provided with inspection sensors for each of the holes on the part which typically could be 80 to 100 in the case of a cylinder head. Typically, however, only one sensor head for each row of holes is required if each hole in the row can be seen during the motion of the part. Thus, one sensor head can do all eight rocker stud holes for a four cylinder head, for example.

While the apparatus is typically located in an inspection area, it can be put into the actual machining lines. In this case it is preferred to provide means to keep the sensor heads clean. For example, the sensor head can have a blow-off nozzle directed down the beam axes which is fed with clean air which provides positive pressure to keep dirt, oil, mist, and coolant spray off the sensor window. Additionally, a shutter may be utilized which is also actuated by force of the blow-off air or alternatively by an external solenoid. In the blow-off air actuated case, the sensor only looks when the air supply is turned on and the shutter is otherwise shut. Such sensors can be typically located between machining operations, as the measurement is actually done on the fly between the fixed machining stations where the part must be stopped. Thus, at the time that the sensors need to be opened and looking, the machining process in the adjacent stations need not be taking place. This is, of course, a benefit since it allows considerable reduction in the amount of spray and mist in the inspection area.

Figure 5:
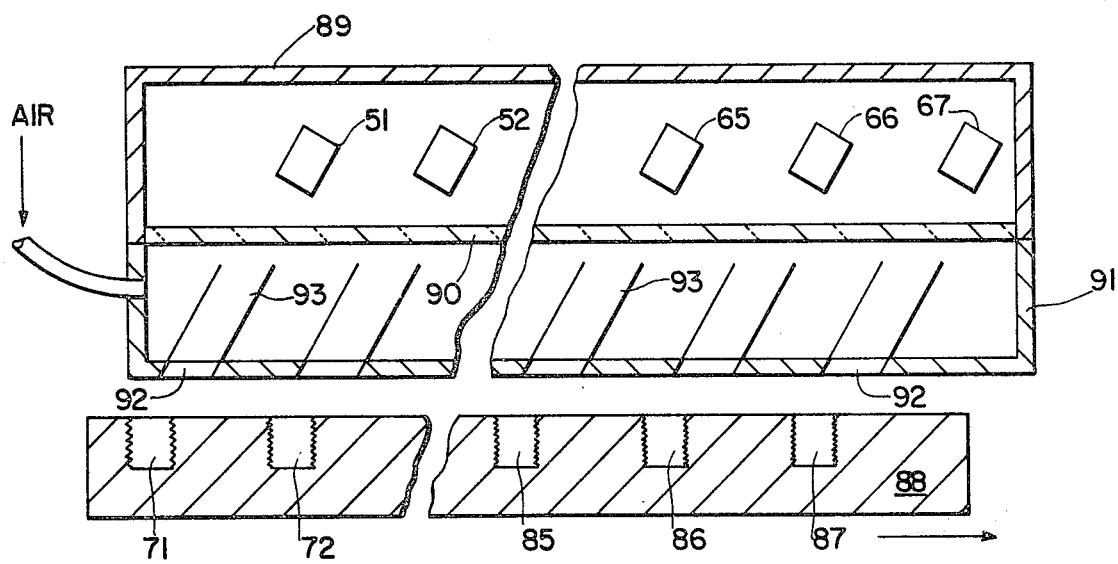
FIG. 5 is a diagrammatic side elevation view of a further embodiment of the invention.

A system for keeping clean a large number of sensors is shown in FIG. 5. In this case, seventeen such thread sensor heads 51 through 67 are arrayed to look at all seventeen of the threaded holes 71-87 on the pan rail face of a transmission case 88. The transmission case is moved through the inspection station on the lift and carry transfer machine (not shown). The sensor heads are mounted in a housing 89 and each points through a protective transparent window 90. A second housing 91 is provided outside window 90 and is provided with a plurality of apertures 92 each of which is aligned with a respective sensor unit to permit the passage of light from the sensor unit light source unit onto part 88 and thence back to the detector unit. Each sensor unit, of course, may be of the type described above in connection with FIGS. 1-3. A plurality of plastic tubes 93 is secured to housing 91 extending from each aperture 92 towards window 90 but spaced therefrom to permit ingress of air supplied into housing 91 from a suitable air supply. A flow of air through and out of each of the tubes 93 is thus provided. This arrangement is quite effective to prevent the accumulation of grease, etc., which can eventually interfere with operation of the sensor units. Housing 91 is secured to housing 89 in any convenient manner and window 90 is preferably easily removed for periodic cleaning. Housing 89 is preferably provided with one or more parts (not shown) which permit visualizing the thread image on the face of the detectorin each detector unit. In each of the various embodiments of the invention, it is preferred to mount the sensor elements in a housing and it is preferred that each such housing be provided with an access port for visualizing the thread image on the face of the detector. It is also preferred to provide such housing with a protective transparent window member through which the sensor unit or units operate.

Systems such as this can go for a long time without required window cleaning maintenance to be done and in any case, it should be noted that the sensor is fail safe in its ability to at least signal a reject if it should go down for any reason. This is an important feature not present in mechanical contact probes which can allow bad parts to go through without any indication that something is wrong with the sensor.

Figure 6:
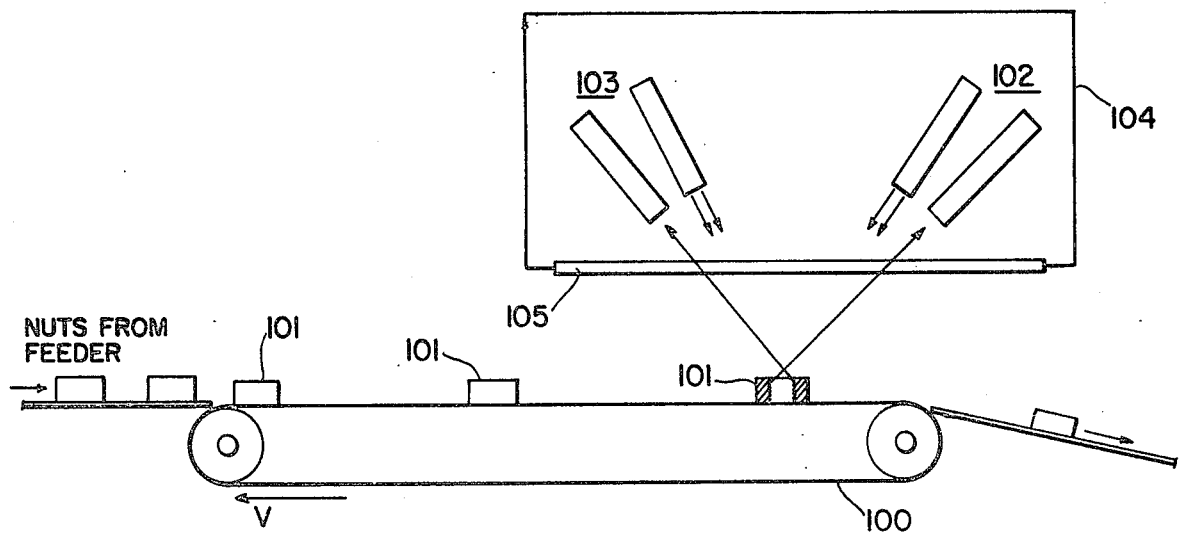
FIG. 6 is a diagrammatic side elevation view of a further embodiment of the invention.

Consider now FIG. 6 which illustrates an embodiment of the invention used to inspect threaded connecting rod nuts. In this case, a driven roller belt 100 carries the nuts 101 single file past two sensor units 102, 103, of the type described above which are mounted in a housing 104 having a window 105 and which are aimed at 180° apart so as to see two zones of the nut internal diameter. In this case, the internal threads are examined and missing threads or out of sequence threads due to crossed threads and wrong pitch nuts are detected. Appropriate reject is provided for bad nuts with a flipper or air solinoid. Pitch is readily determined by comparison of belt speed to thread signal frequency. In this and other embodiments where velocity of the relative movement between the part and the sensor unit, it is preferable to provide means for monitoring the velocity of the movement. This is readily accomplished by suitable velocity measuring devices. In a sophisticated arrangement, the monitored velocity data would be utilized where appropriate such as in the case just mentioned and in the timing of the actuating and/or deactuating of the sensor units.

Figure 7:
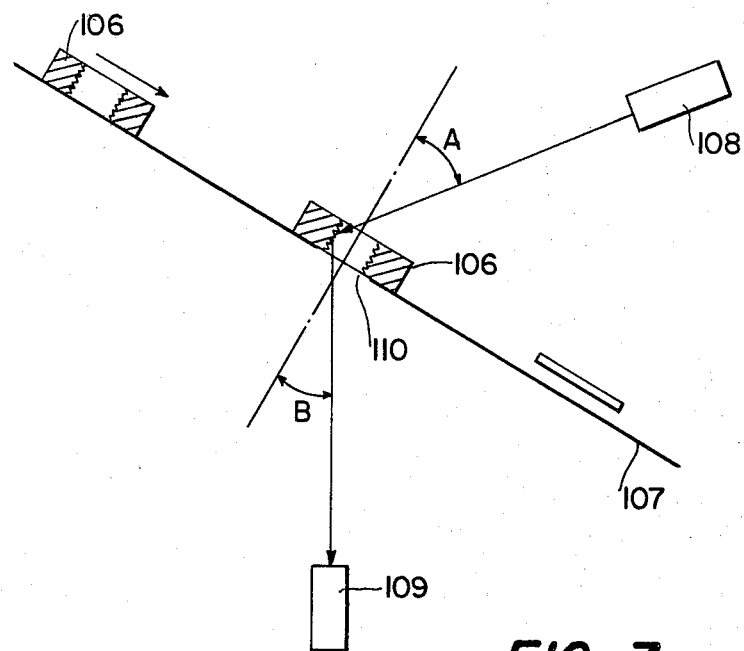
FIG. 7 is a diagrammatic side elevation view of a further embodiment of the invention.

The above systems have all utilized measurement of thread image forms in reflection. This is the preferred arrangement since it results in a one sided sensor and can be used with moving parts on conveyor belts, etc. Quite clearly, it is also the only version that can be used with blind holes. And too, no dirt from the parts or environment generally lands on the window since it usually points downwardly. That is not to say, however, that the invention cannot be used in a transmission mode and FIG. 7 illustrates this case on nuts 106 sliding down a track 107. A light source unit 108 similar to that described above is provided above track 107 to illuminate the threads and a detector unit 109 is provided below the track to receive the transmitted light. An opening 110 is provided in track 107 at the inspection location. Typically, in this case, acute angles A and B can be of the same magnitude. In this embodiment, it is the thread crests, often flat, that create the peak values of the reflected light rather than the thread flanks as in reflection. It should also be noted that while the above examples have all shown the part in motion relative to the sensor head fixed with respect to the Earth, the opposite is also true; the part can be stationary and the sensor head moved. This, is for example, can be the case in doing the end threads on an engine block where it is easier to move the sensors across the front of the block than it is to move the block sideways. The same is true on the flywheel bolt holes on a crankshaft where the head is moved circularly. It is also possible, of course, to move both the sensor unit and the part provided that there is relative movement therebetween.

In observing threads whose axes are horizontal on machining lines where there is coolant in the threads, it is not a good idea to look at the thread form at the bottom of the hole but rather at the sides or the top of the hole. Inspecting the sides in particularly convenient since the part is generally in motion such that it provides a scan of the side of the threaded hole. It should be noted that these comments apply to threaded holes which are on the sides of the part in a horizontal position. Most applications fit this arrangement on the machining lines but holes can also be on the top as well. Where the threaded holes are on the top, a particular problem exists with water in the holes at least if coolant is used such as in machining aluminum. There is no effective way to deal with this other than blow the water out of the holes and the present apparatus can readily be provided with conventional means for doing that. In general, it is desirable to blow all the holes anyway before passing them through such an inspection station.

In many applications such as those described above, it is further desirable to check the small holes put into the part at various drilling stations. The smaller the hole, the more difficult it is to probe it with mechanical means and the more easy it is for the drills to break off thereby causing a problem.

Even where mechanical probes can be used, there is great difficulty with the probes themselves getting bent or broken. Generally, in this case, the probe actuates but since it never goes into the hole because it is bent, it thinks the hole is quite clear. Such arrangements are clearly not fail safe. The optical sensors for probing holes, either of the threaded type mentioned above or for clear holes now to be described, does not have this problem and if anything fails, such as the light source, the detector amplifier, the window getting too dirty, or what have you, it will reject parts. This forces operators to pay attention to the problem and has a benefit to productivity.

Inspection of blind holes is considerably more difficult and generally utilizes a light source and detector placed as in FIG. 1 but oriented more along the axis of the hole rather than at the thread face angles. This then looks for the characteristic light/dark/light signal of the surface of the part into the hole and back out to the surface as an indicator that a hole is there and this is quite useful on dowel holes and water jacket holes and other similar blind holes in cylinder heads, etc.

Figure 8:
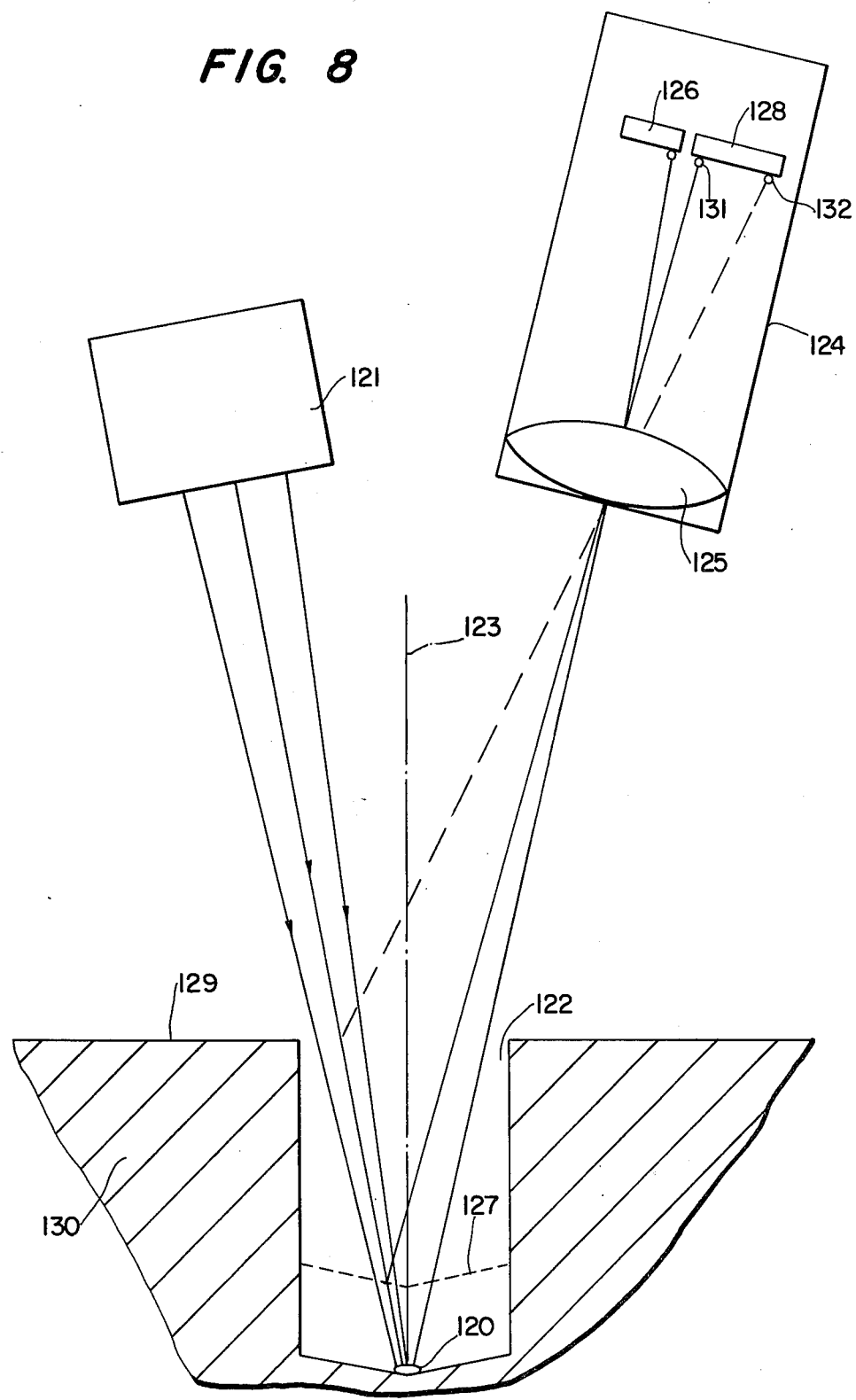
FIG. 8 is a diagrammatic side elevation view of a further embodiment of the invention.

Naturally, many blind holes need to be inspected before tapping, and failure to do so risks tap breakage. To do this, one needs to know in the simplest case only that a hole is there, obtained easily from a light/dark/light indication as above. However, it is obviously of interest to know the depth of the hole as well. This can be seen by actually looking for the shift in position of a spot projected down the hole. For example, consider FIG. 8. In this case a light spot 120 is projected from light source 121 into hole 122 typically but not necessarily at an angle to the hole axis 123. Light source 121 is preferably a laser, focused LED, or a focused white light using an aperture to define the source size and therefore the image spot size.

At an angle a detector unit 124 views the spot projected onto the bottom of the hole. A lens 125 forms the spot image onto a detector 126 to cause an accept signal. If, however, the hole is shallow as shown by dotted lines 127, the image shifts and misses detector 126. If desired, a further detector 128 may be provided to detect the spot image of holes less than a desired depth. Detector 128 may also serve to detect the absence of a hole since, if the spot is formed at the surface 129 of the part 130. In the arrangement shown in FIG. 8, the spot from a shallow hole detected by detector 128 is denoted 131 and the detected spot where no hole is present is denoted 132.

Clearly, the unit can work in reverse, wherein the detector is set up to view the spot when shallow, but this is not fail safe as a lack of light can be caused by other factors such as a bulb failure, etc.

Finally, a two (or more) detector system can be used wherein the balance of detectors is compared. This allows compensation for total power returned.

It is an advantage of the invention that the light source and light detector elements can be located a substantial distance from the part undergoing inspection. This arrangement minimizes the likelihood of damage. It is therefore preferred that these elements be located a substantial distance from the part undergoing inspection and, particularly for large parts, a distance of at least two inches is preferred.

It is further noted that the light from the light source of this invention is only required in the zone where the imaging lens axis intersects the thread surface. In the example of FIG. 1, the field from light source 13 must be broad enough to cover several threads, since the thread axis is perpendicular to the direction of motion and the zone of intersection shifts up and down.

In the example of FIG. 4, however, showing inspection of an end hole whose axis is parallel to the direction of motion, the point of intersection of the lens axis with the thread is relatively invariant. In this case, a much more spot type light source could be used.

Besides incandescent bulbs, solid state LEDs and solid state CW lasers are desirable sources, with long life, low power requirements and no heat dissipation problems. However, reliable versions of the latter are quite expensive at the present time and LEDs often do not have sufficient power to overcome part reflectivity losses unless more sophisticated signal detection is used. In addition, these solid state sources are infra red and are relatively hard to initially align, even with the aid of sniper scopes and the like.

Gas lasers, such as the 6328 Hene gas laser can be used, but suffer a substantive probe disadvantage relative to inexpensive incandescent sources.

A typical sequence of events in the method of the invention includes the following:

1. A part present sensor provides a voltage command to enable a counter.

2. The counter circuit analyzes the quasi-periodic waveform which comes from the sensor unit detector and determines the number of positive (or negative) going signals above (or below) a pre-set voltage Vo.

3. If required, the count process is deactivated on signal from a second part present sensor or from a timer indicating that the threaded portion of interest has passed the sensor zone.

4. The counter value so obtained is compared on a comparison circuit to a stored value for that part (e.g. a minimum number of threads).

5. If the threads counted exceed the stored value, the threaded hole or object is determined to be good and allowed to pass. If not, a reject command signal may be given to reject the part by automation. A signal may also be given to mark the part.

If a timer is used for step 3, part speed is assumed sufficiently constant from part to part. If not, a separate part speed motion sensor can provide a correction signal. Alternatively, the count process can be deactivated by another part present sensor (or simply a signal from the first sensor) indicating that the rear end of the part or other feature has passed.

Note that step 2 can alternatively incorporate an additional circuit to vary the value of Vo as a function of light received, either overall light from all threads or a floating value $V_f$ relatively proportional to the envelope of thread energy.

Figure 9:
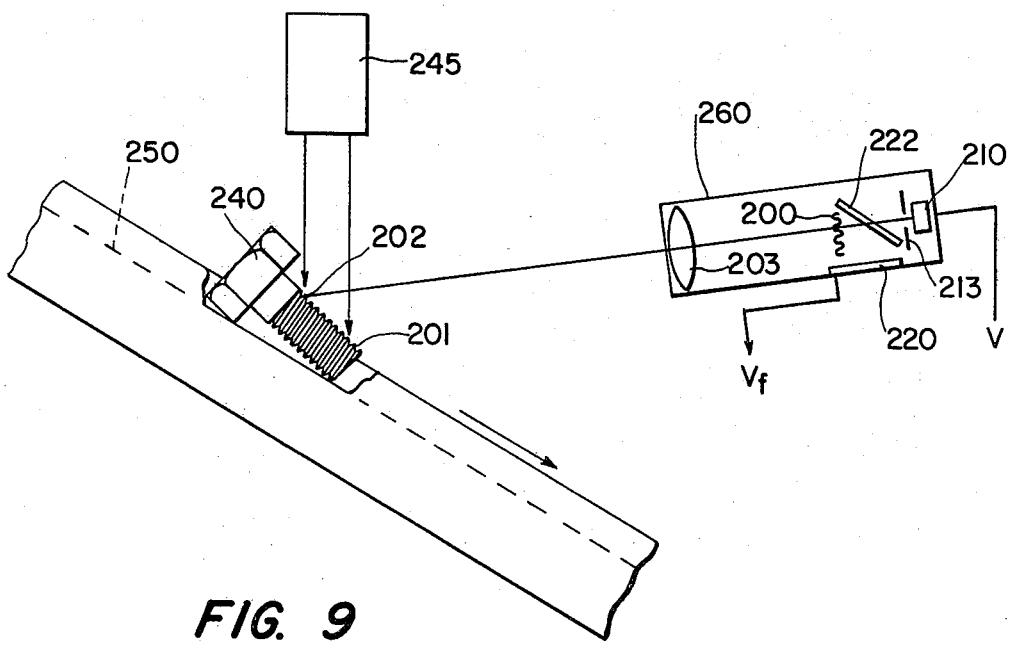
FIG. 9 is a diagramnmatic side elevation view of a further embodiment of the invention.

Such floating threshold value can also be generated optically as shown in FIG. 9. In this case, the total image 200 of threads 201 in the region of the immediate thread point 202 viewed on the axis of lens 203 by detector 210 having aperture 213 impinges on a second detector 220 via beam splitter 222. The output of detector 220 is used to generate the instantaneous threshold voltage $V_f$ used in the count circuit for the thread signal produced by detector 210.

With reference to FIG. 9, a bolt 240 illuminated by light source 245 is shown being inspected for the number of threads present as it moves downward on Vee track 250, which constrains the round head and threaded shank in relative alignment to the thread sensing system. If a moving flat belt such as that of FIG. 6 were to be used, it is clear that the shank would be oriented at arbitrary though small angles since clearance would have to be provided for the head by rails used to align the bolts. In this case, it is of particular importance that a floating threshold be used, as the reflected thread image can vary widely in intensity as the screwed part goes through the measuring zone. The same is also true for nuts or any other part whose location can vary side to side as it passes through.

FIG. 9 also illustrates a much larger included angle between the light source 245 and detector unit 260 than is possible with blind holes in parts. In the case shown, where each is on the opposite side of the normal to the part centerline, the shadowing effect is much like that of FIG. 7, though the direction of motion of the threads is 90° to that of the nut in FIG. 7.

A further advantage of the floating threshold approach shown in FIG. 9 is that it automatically compensates for lamp degradation and dirty windows, the two most common problems in plants.

What is claimed is:

1. Apparatus for inspecting threaded objects comprising:

light source means for illuminating threads of a threaded object;

lens means for forming an image of at least a portion of the threads of a threaded object illuminated by said light source means;

means for detecting said image, said detecting means comprising a light sensitive member having a light sensitive area sufficiently small to resolve the individual threads in the image of the threads of an illuminated threaded object, said light sensitive member having an output signal responsive to light incident on said light sensitive area; and means for analyzing said output signal to determine the quality of the threads of the threaded object.

2. Apparatus according to claim 1 wherein said light source means comprises an incandescent lamp.

3. Apparatus according to claim 2 wherein the incandescent lamp comprises a filament.

4. Apparatus according to claim 3 wherein the incandescent lamp comprises a clear glass envelope.

5. Apparatus according to claim 2 wherein said light source means comprises lens means for focusing an image of at least a portion of said filament on at least a portion of the threads of a threaded object.

6. Apparatus according to claim 1 further comprising a transparent protective member interposed between, on the one hand, a threaded object and, on the other hand, said light source means, said lens means, and said image detecting means.

7. Apparatus according to claim 6 wherein each of said light source means, said lens means, and said image detecting means are mounted in a housing, said transparent protective member forming a window in said housing.

8. Apparatus according to claim 1 wherein said image detecting means comprises a photodiode.

9. Apparatus according to claim 1 wherein said image detecting means comprises a mask member adjacent said image detecting means having an aperture sufficiently small to resolve the image of the threads of an illuminated threaded object.

10. Apparatus according to claim 9 wherein said mask aperture is curved to approximate the curvature of the thread image.

11. Apparatus according to claim 1 wherein said image forming lens means comprises a lens having a focal length of 50 to 150 mm.

12. Apparatus according to claim 1 further comprising means for locating a threaded object in a thread inspection location in which location the threads of the threaded object are illuminated by said light source means.

13. Apparatus according to claim 12 wherein said image forming lens means is located at least two inches away from the threads of a threaded object located in said threaded inspection location.

14. Apparatus according to claim 12 further comprising means for providing relative motion between said threaded object and said image detecting means.

15. Apparatus according to claim 14 wherein said relative motion means comprises a powered roller conveyor.

16. Apparatus according to claim 14 wherein said relative motion means comprises a driven conveyor belt.

17. Apparatus according to claim 14 further comprising means for actuating said analyzing means when the threads of said threaded object are moved into said thread inspection location.

18. Apparatus according to claim 17 wherein said actuating means comprises means for deactuating said analyzing means when the threads of said threaded object are moved out of said thread inspection location.

19. Apparatus according to claim 17 wherein said actuating means comprises means for sensing the position of a threaded object.

20. Apparatus according to claim 19 wherein said actuating means comprises a plurality of said sensing means.

21. Apparatus according to claim 1 for inspecting a plurality of discrete threaded holes in a unitary object comprising a plurality of thread sensing units, each of said thread sensing units comprising said light source means, said lens means, and said image detecting means.

22. Apparatus according to claim 21 wherein said thread sensing units are mounted in a common housing, said housing having a transparent protective member forming a window in said housing.

23. Apparatus according to claim 22 further comprising means for keeping said window clean.

24. Apparatus according to claim 1 wherein said analyzing means comprises means for determining the number of said threads.

25. Apparatus according to claim 12 wherein said light source means, said lens means, and said image detecting means are positioned on one side of said thread inspection location whereby the bright portions of the thread image are formed by light reflected from the flanks of the threads positioned in said thread inspection location.

26. A method for inspecting threaded objects comprising:

providing a sensor unit, said sensor unit comprising light source means for illuminating threads of a threaded object, lens means for forming an image of at least a portion of the threads of a threaded object illuminated by said light source means, and means for detecting said image, said detecting means comprising a light sensitive member having a light sensitive area sufficiently small to resolve the individual threads in the image of the threads of an illuminated threaded object, said light sensitive member having an output signal responsive to light incident on said light sensitive area;

moving a threaded object relative to said sensor unit such that the light from said light source means illuminates said threads whereby an image of at least a portion of the threads illuminated by said light is formed by said lens means, and is incident upon said detecting means whereby said output signal is produced; and analyzing said output signal to determine the quality of said threads.

27. A method according to claim 26 wherein said threaded object comprises a plurality of discrete threaded portions and wherein sad discrete threaded portions are moved sequentially relative to said sensor unit whereby a single sensor unit is utilized to inspect said plurality of discrete threaded portions.

28. A method according to claim 26 further comprising the steps of initiating said output signal analysis substantially at the time that said thread image is first incident upon said light sensitive member and terminating said output signal analysis substantially at the time that said thread image is last incident upon said light sensitive member.

29. A method according to claim 28 including the step of sensing the position of the threaded object to initiate said output signal analysis and to initiate a timer for terminating said output signal analysis.

30. A method according to claim 28 wherein the steps of sensing the position of the threaded object at a first position to initiate said output signal analysis and sensing the position of the threaded object at a second position to terminate said output signal analysis.

31. Apparatus for detecting the presence and for determining the depth of a blind hole comprising:

light source means for projecting a spot of light onto the surface of an object and onto the bottom of a blind hole in said surface;

lens means for forming an image of said spot of light;

detector means for detecting said image, said detector means comprising a first light detector positioned to detect the image of said spot of light on said surface and a second light detector positioned to detect the image of said spot of light on the bottom of said blind hole, said first and second light detectors each having an output signal responsive to light incident thereon; and means for analyzing the output signal of said first light detector to determine the presence of said hole and for analyzing the output signal of said second light detector to determine the depth of said hole.

32. Apparatus according to claim 31 wherein said second light detector comprises a light sensitive element positioned to detect the image of said spot of light in the bottom of said blind hole, only in the event that the depth of a blind hole onto the bottom of which said spot is projected is at least a pre-determined depth.

33. A method of detecting the presence of and for determining the depth of a blind hole in an object comprising:

providing a sensor unit, said sensor unit comprising light source means for projecting a spot of light onto the surface of an object and onto the bottom of a blind hole in said surface, lens means for forming an image of said spot of light, and detector means for detecting said image, said detector means comprising a first light detector to detect the image of said spot of light on said surface and a second light detector positioned to detect the image of said spot of light on the bottom of said blind hole, said first and second light detectors each having an output signal responsive to light incident thereon;

moving an object having a blind hole in a surface thereof relative to said light source whereby said spot of light is first incident upon said surface on one side of said blind hole then incident upon the bottom of said hole, and then incident upon said surface on the other side of said blind hole;

analyzing the output signal of said first detector to determine the presence of said hole in said surface; and analyzing the output signal of said second detector to determine the depth of said hole.

* * * * *